United States Patent
Nadig et al.

(10) Patent No.: US 11,344,025 B2
(45) Date of Patent: May 31, 2022

(54) ORGAN PRECONDITIONING FORMULATION WITH MITOCHONDRIAL ELONGATING AGENTS

(71) Applicant: MUSC FOUNDATION FOR RESEARCH DEVELOPMENT, Charleston, SC (US)

(72) Inventors: Satish N. Nadig, Johns Island, SC (US); Carl Atkinson, Mt. Pleasant, SC (US); Danh T. Tran, Charleston, SC (US)

(73) Assignee: MUSC FOUNDATION FOR RESEARCH DEVELOPMENT, Charleston, SC (US)

( * ) Notice: Subject to any disclaimer, the term of this patent is extended or adjusted under 35 U.S.C. 154(b) by 175 days.

(21) Appl. No.: 16/339,179

(22) PCT Filed: Dec. 26, 2018

(86) PCT No.: PCT/US2018/067477
§ 371 (c)(1),
(2) Date: Apr. 3, 2019

(87) PCT Pub. No.: WO2019/133586
PCT Pub. Date: Jul. 4, 2019

(65) Prior Publication Data
US 2020/0281190 A1 Sep. 10, 2020

Related U.S. Application Data

(60) Provisional application No. 62/647,017, filed on Mar. 23, 2018, provisional application No. 62/611,706, filed on Dec. 29, 2017.

(51) Int. Cl.
*A01N 1/02* (2006.01)
*C07C 251/86* (2006.01)
*C07D 239/95* (2006.01)

(52) U.S. Cl.
CPC .......... *A01N 1/0226* (2013.01); *C07C 251/86* (2013.01); *C07D 239/95* (2013.01)

(58) Field of Classification Search
None
See application file for complete search history.

(56) References Cited

U.S. PATENT DOCUMENTS

2005/0038051 A1  2/2005  Nunnari et al.
2012/0294956 A1  11/2012  Qian et al.

FOREIGN PATENT DOCUMENTS

WO  2017019214 A1  2/2017

OTHER PUBLICATIONS

The International Search Report and Written Opinion, dated Mar. 27, 2019, in the corresponding PCT Appl. No. PCT/US18/67477.
Asalla et al. "Restoring Mitochondrial Function: A Small Molecule-mediated Approach to Enhance Glucose Stimulated Insulin Secretion in Cholesterol Accumulated Pancreatic beta cells", Scientific Reports. 2016. vol. 6:27513, 17 pages, entire document, especially: p. 11, Figure 6A; p. 11, Figure 6B, Small molecule M1.

*Primary Examiner* — Joseph R Kosack

(57) ABSTRACT

Provided herein is a formulation to pre-treat an organ prior to transplantation and for inducing mitochondrial morphological alterations.

5 Claims, 8 Drawing Sheets

White: isotype control

Blue: unactivated untreated cell control

Gray: unactivated M1/Mdivi1-treated cell control

Black: activated untreated cells

Red: activated M1/Mdivi1-treated cells

ORGAN PRECONDITIONING FORMULATION WITH MITOCHONDRIAL ELONGATING AGENTS

CROSS-REFERENCE TO RELATED APPLICATIONS

This application is a National Stage Application of PCT/US2018/067477 filed on Dec. 26, 2018, which claims priority from U.S. Provisional Patent Application No. 62/611,706 filed on Dec. 29, 2017 and U.S. Provisional Patent Application No. 62/647,017 filed on Mar. 23, 2018. Each of prior mentioned applications is hereby expressly incorporated by reference herein in its entirety.

STATEMENT REGARDING FEDERALLY SPONSORED RESEARCH OR DEVELOPMENT

This invention was made with Government support under grant numbers AI142079, NIH/NIBIB K08 EB019495-01A1, NIH/MSTP T32 GM008716-17, NIH/NHLBI T32 HL007260-40, and NIH/NHLBI T32 HL007260-41. The Government has certain rights in the invention.

FIELD OF THE INVENTION

The invention is directed to a formulation and method to pre-treat an organ prior to transplantation and to a formulation for inducing mitochondrial morphological alterations. The formulation comprises a therapeutically effective amount of mitochondrial elongating agents.

All publications, patents, patent applications, and other references cited in this application are incorporated herein by reference in their entirety for all purposes and to the same extent as if each individual publication, patent, patent application or other reference was specifically and individually indicated to be incorporated by reference in its entirety for all purposes. Citation of a reference herein shall not be construed as an admission that such is prior art to the present invention.

BACKGROUND OF THE INVENTION

Transplantation is a widely accepted and highly successful therapy for end-stage organ disease. While success rates and survival have risen steadily, due largely to improved immunosuppression regimes, there is a growing appreciation that factors that occur early in the life of the graft, significantly affect long-term survival. The donor organ is exposed to a series of injurious events prior to and during the transplant operative period: brain death, cold storage, cold and warm ischemia reperfusion, which damage and immunologically prime the donor organ for alloimmune recognition. The removal, storage, and transplantation of a solid organ from a donor profoundly alters the homeostasis of the interior milieu of the organ. These effects manifest in the degree to which the return of normal organ function is delayed or prevented after transplantation is completed. The injury an organ sustains during recovery, preservation, and transplantation occurs primarily as a result of ischemia and hypothermia. Techniques for organ preservation serve to minimize this damage to promote optimal graft survival and function.

Damage to donor organs prior to transplantation occurs in 2 main phases. The first, cold ischemic phase, occurs when the organ flushed in situ then procured and preserved in a static or pulsatile hypothermic state prior to transplantation into the recipient. The second, warm ischemic phase, includes the time from where the organ is removed from the preservation solution and sewn into the recipient. Techniques for organ preservation serve to minimize this damage to promote optimal graft survival and function. As most transplanted organs are from deceased donors, the organ must inevitably be stored after its removal from the donor until it can be transplanted into a suitable recipient. The donor and recipient are often in different locations (sometimes even when organs are harvested from living donors), and time is therefore needed to transport the donor organ to the hospital where the recipient is being prepared for transplantation.

Acceptable preservation times vary with the different organs. Most surgeons prefer to transplant the heart and lungs within 5 hours of removal; kidneys can safely be stored for 24-48 hours, but earlier transplantation is preferred. Most pancreas transplants are performed after 5-15 hours of preservation. Liver transplants usually are performed within 6-12 hours. Over the last 20 years, a number of methods and solutions have been developed to preserve donor organs for transplantation. Collins et al first introduced the simple cold-storage technique to store and transport kidneys up to 30 hours. The development of the University of Wisconsin cold-storage solution (UW-CSS) in 1986 improved organ preservation and resulted in a better understanding in preservation related injury. Various preservation solutions exist, each substantially differs in their composition, but the purposes of each are similar: to prevent cellular edema, to delay cell destruction, maintain organ metabolic potential, and to maximize organ function after perfusion is re-established. Commonly used solutions include: University of Wisconsin (UW) solution, Kyoto ET Solution, Celsior Solution, Phosphate Buffered Sucrose Solution, Bretschneider Histidine Tryptophan Ketoglutarate (HTK) Solution, Ross-Marshall Citrate Solution, Euro-Collins Solutions, and Perfadex. Different solutions are used for different organs, such as Perfadex for the lung, and different solutions are preferred at different institutions. The most widely utilized preservation solution is the University of Wisconsin (UW) solution, which was developed for heart, liver, kidney, and pancreas preservation. It is considered the standard for cardiac, renal, pancreas, and hepatic preservation, effectively extending the ischemic time for these organs and allowing them to be transported considerable distances to waiting recipients. The composition of the solution is complex. The solution has an osmolality of 320 mmol/kg and pH 7.4 at room temperature and is composed of the following: Potassium 135 mmol/L, Sodium 35 mmol/L, Magnesium 5 mmol/L, Lactobionate 100 mmol/L, Phosphate 25 mmol/L, Sulphate 5 mmol/L, Raffinose 30 mmol/L, Adenosine 5 mmol/L, Allopurinol 1 mmol/L, Glutathione 3 mmol/L, Insulin 100 U/L, Dexamethasone 8 mg/L, Hydroxyethyl starch (HES) 50 g/L, and Bactrim 0.5 ml/L. The components of UW solution, as with the other aforementioned solutions, are utilized to prevent cellular edema, cell destruction, maintain organ metabolic potential, and to maximize organ function after perfusion is reestablished. They do nothing to modulate the immunological injury suffered as a consequence of organ donation, nor do they prepare the donor organ for the oncoming immunological attack by the recipient immune system.

Central to these immunological insults is the activation of donor endothelial cells (ECs) which are semi-professional antigen-presenting cells (APCs) that sit at the interface between donor graft and recipient immune system. Upon brain death, organ procurement, organ preservation and reperfusion, ECs promote inflammation, cytokine and chemokine release to recruit innate immune cells and alloreactive memory T-cells that mediate graft damages. It is becoming increasingly appreciated that modulation of the endothelium prior to transplantation may improve graft outcomes. Recent studies have shown that modulating mitochondrial morphology alters the function of immune cells, including T-cells and professional APCs like dendritic cells.

In contrast to the historical belief that mitochondria are sausage-shaped organelles, they constantly fuse into tubular networks or divide into small rounded structures. Morphological changes of mitochondria regulated by the fusion/fission process appear to play important roles in the immune synapse during APC-T-cell interaction. Immune synapse is normally formed to facilitate signaling efficiency important for T-cell activation. During this process, mitochondria translocate to the immune synapse in a cytoskeleton-dependent fashion to provide energy to ATP-consuming processes and to maintain calcium flux for T-cells. Mitochondrial translocation to immune synapses has also been observed in other immune cells, including NK cells and B-cells. In fact, during T-cell and B-cell interaction for antigen presentation, cellular polarization toward the immune synapse occurs in B-cells, and additional evidence indicates that mitochondria are localized to the synapse in the APC to provide energy and maintain calcium flux during antigen presentation.

For mitochondria to efficiently translocate, they need to move as small organelles instead of as large networks and the fusion protein MFN2 can make mitochondria become stationary by tethering them to the endoplasmic-reticulum. On the other hand, the fission protein DRP1 is required for mitochondrial positioning and localization at the immune synapse in T-cells. Mitochondrial elongation and network formation can be facilitated with the combo drugs M1 (fusion promoter) and Mdivi1 (fission inhibitor). In organ transplantation, one would hypothesize that elongating mitochondria in ECs with M1/Mdivi1 leads to inefficient mitochondrial translocation and thus inefficient activities at the immune synapse, causing ECs to fail to activate alloreactive T-cells. To date there have been no published studies investigating mitochondrial fusion/fission in the allograft before or during cold storage, or following reperfusion. However, in the heart in the non-transplant setting, inhibiting mitochondrial fission with Mdivi1 has been reported to protect both myocardium and microvasculature from the detrimental effects of focal IRI.

Therefore, a need exists in the art for novel additives to standard organ preservation solutions to prevent donor organ endothelial and epithelial activation, cytokine release, impair immune co-stimulation, and, thereby, reduce graft injury.

SUMMARY OF THE INVENTION

The present invention is directed to a formulation to pre-treat an organ prior to transplantation, comprising:
a) a first composition comprising a therapeutically effective amount of compound M1 of formula:

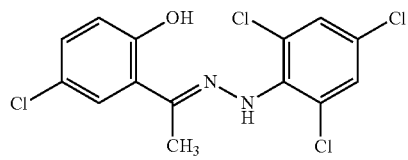 [SMILES: C/C(=N\Nc1c(Cl)cc(Cl)cc1Cl)c1cc(Cl)ccc1O]

and a therapeutically effective amount of compound Mdivi1 of formula:

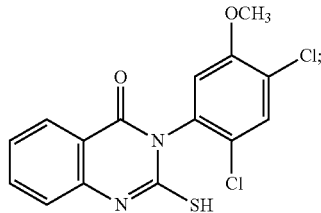 [SMILES: COc1cc(-n2c(S)nc3ccccc3c2=O)c(Cl)cc1Cl]

and
b) a second composition comprising a preservation solution or a warm perfusate.

The invention is further directed to a method of pretreating an organ prior to transplantation with said formulation; a formulation for inducing mitochondrial morphological alterations; and to a kit for producing the formulation.

DETAILED DESCRIPTION OF THE INVENTION

Figure 1:
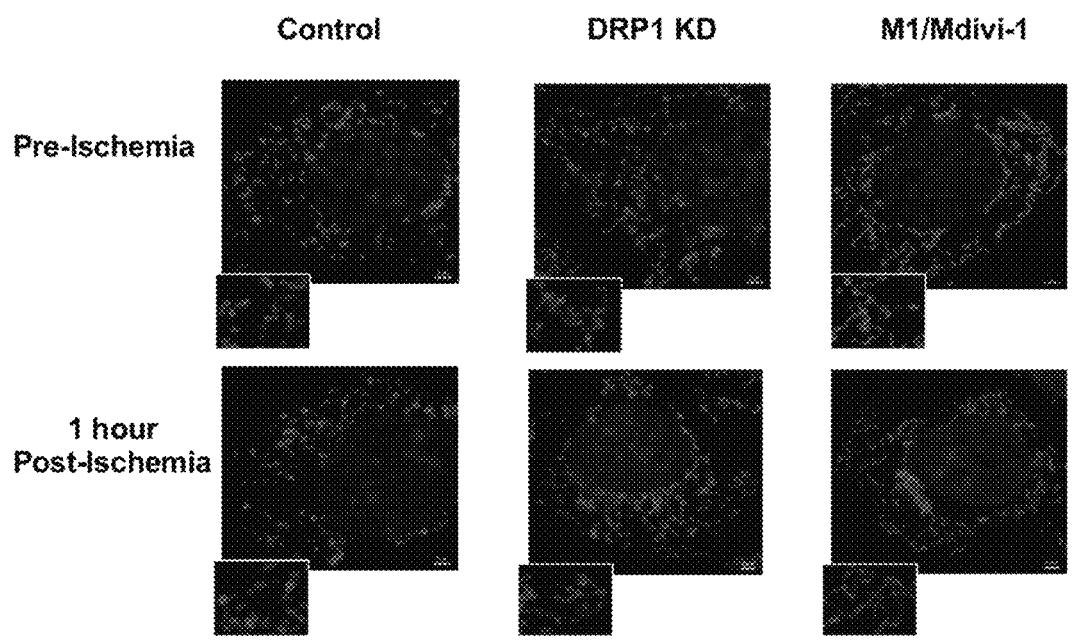
FIG. 1 shows control, DRP1-KD and M1/Mdivi-1 treated MCECs stained for mitochondria (red) and nucleus (blue) and imaged with confocal microscopy. DRP1-KD and M1/Mdivi-1 have elongated mito which persist post CIT.

The invention provides for the addition of M1/Mdivi1 to standard organ preservation solutions to prevent donor organ EC activation, cytokine release, impair immune co-stimulation, and thereby reduce graft injury. The use of such an additive to a standard preservation solution will lead to the development of a first in class priority preservation solution for broad application to all solid organ transplants. In addition, with the increasingly common utilization of normothermic machine perfusion, such as the Organ Care System developed by TransMedics, adding M1/Mdivi1 to the warm perfusate to precondition donor organs prior to transplantation promises a new novel approach to facilitate graft tolerance induction.

In an in-vitro model, the inventors have shown pretreating cardiac ECs with M1/Mdivi1 to promote mitochondrial elongation and network formation reduces the release of cytotoxic agents by co-cultured sensitized allogeneic T-cells. The fusion promoter/fission inhibitor combo agents M1/Mdivi1 can be delivered directly to the donor endothelium prior to transplantation as an additive constituent of standard organ preservation solutions or as an additive constituent of warm perfusates in normothermic machine perfusion. The delivery mode of the agents will be engineered in such a way as to enable it to penetrate endothelial cells to protect them from ischemia reperfusion injury, and also promote endothelial tolerance. In this format, the agents can be used in multiple organ preservation solutions and/or warm perfusates, so that it can have a broad application to all solid organ transplants.

Organ transplantation ("Tx") has evolved steadily and is the treatment of choice for organ failure. While Tx has extended many lives, there is still need for significant improvement.

Within the first year after Tx, 50-80% of patients experience 1-3 episodes of rejection, and while immunosuppressive agents have improved, long-term graft survival has not. Chronic rejection (CR) remains a roadblock to allograft longevity placing further burden on the current organ shortage. There is, however, an untapped window of opportunity to ameliorate many of these current problems. Injury to the allograft occurs early in the Tx and often occurs before implantation, via donor brain death (BD) and donor organ storage; therefore, "pretreating" the organ prior to implantation rather than simply "preserving" the organ may blunt the early insults incurred upon the graft, thereby abating the long-term consequences. As part of the Tx procedure, the donor organ is stored at 4° C. most commonly in University of Wisconsin (UW) solution. This process, while essential, subjects the graft to cold ischemia and warm ischemia reperfusion injury (IRI). During Tx, endothelial cells (ECs) sit at the interface between the donor allograft and the recipient immune system. As the integrity of the endothelium is compromised by IM, a cascade of events results in EC activation, recruitment and programming of recipient immune cells, acute rejection, allograft vasculopathy (AV), and graft loss. Additionally, in the current standard of care, immunosuppressive agents successfully target effector T cells, while sparing alloreactive memory T-cells, which remain a barrier to Tx tolerance. Current immunosuppressive strategies also harbor a significant side-effect profile including, diabetes, cardiovascular disease, and cancer, often limiting patient survival. Therefore, strategies that target memory cells and reduce the burden of standard of care immunosuppression are urgently needed.

ECs play a central role in priming and inducing proliferation of these alloreactive memory T-cells, and thus strategies to minimize EC activation and damage are urgently needed to reduce these early injurious events. Current management guidelines focus on peri- and post-operative treatments for the Tx recipient with high doses of potent immunosuppression, rather than preconditioning the graft against IRI and subsequent rejection. The studies proposed here seek to investigate strategies to precondition the donor ECs pre-Tx, such that they reduce EC injury, activation and immunogenicity. Recent studies have shown that mitochondria (mito) are dynamic organelles that not only power the cells energy requirements but also play key roles in steering the immune phenotype of the cell. Here, for the first time, the inventors propose novel studies to define the impact of cold storage and IRI on shaping EC mito morphology and seek to determine how changes in mito shape within the EC can impact these key APCs. The proposed studies will be the first to define the impact of IRI, associated with organ preservation and reperfusion, on mito morphology in ECs, and will further, elucidate the relationship between mito fission and fusion on the immunologic phenotype of ECs. The mechanisms of how mito EC preconditioning in the preservation phase of Tx leads to a decrease in the immunogenicity of the allograft has not been studied previously and serves as the scientific premise explored in this proposal. This proposal is significant in that ECs have not been studied in the context of immunogenicity and mito morphology that would allow for a therapeutic option prior to transplantation. The proposed pretreatment strategy sets the stage for a paradigm shift in the current standard of care during allograft transplantation.

Many of the current standards of Tx practice have not changed in decades, including the use of hypothermic preservation solutions to transport organs and immunosuppressive regimens. Various methods have been utilized to improve the longevity of organs and patients, while trying to inhibit early and late rejection responses. One such strategy that is gaining momentum, and is the focus of this proposal, is the modification of the donor organ pre-Tx as a means to tackle the early unmet needs including: 1) IRI; 2) early graft immune priming; and 3) minimization of standard of care immunosuppression. While necessary for graft survival current immunosuppressive regimens are often toxic to the very organs they are used to protect and subject patients to severe, and sometimes fatal, off-target effects. Therefore, strategies that can control early injury and facilitate immunosuppressive sparing regimens are urgently needed in solid organ Tx.

With the more widespread use of donor organ machine perfusion, comes the opportunity to delivery therapeutics to the allograft pre-Tx, so as to improve post-Tx outcomes. In these systems, the donor organ is preserved ex-vivo for a period of time (preservation phase) prior to implantation. During this time, ECs can be targeted with therapeutics that may prepare them for the onslaught of IRI. The role of ECs in IRI and immune priming is well established and is known to predispose the organ to late graft failure. The event of ischemia itself leads to permeability of the endothelium and adhesion molecule expression, which allows for the infiltration of alloreactive T cells. Interestingly, standard anti-lymphocyte immunosuppression regimens, given at the time of the Tx, often spare memory T cell populations which are recruited and programmed by activated donor ECs to begin a cascade of damage. Infiltration of memory T cells disrupts the normal intercellular gap and tight junctions leading to increased permeability, tissue edema and injury. The ability of primed ECs to aggressively present antigen is controlled at the level of the organelles. Recent studies have established that the mitochondria do more than simply generate energy for cell function. The plasticity of mitochondria is directly correlated to their coordination of cellular function. Fusion and fission of the organelle is tightly controlled by specific peptides that respond to the stressors of the surrounding milieu. Dynamin related peptide (Drp1) is the dominant peptide known to constrict the mito double membrane and induce fission of one organelle into two. Fusion of the outer mito membrane is regulated by Mfn 1 and 2, while the inner membrane is fused by Opa1. These proteins are dependent on the real-time cellular environment. Under times of stress, such as ischemia, fusion allows mitochondria to distribute their resources sharing the electron transport chain and ATP production. Newer data has revealed that the enhanced ability of APCs to present foreign antigen in the setting of inflammation is, in part, controlled by the shape and location of mitochondria within the cell. During T cell activation, APCs present peptide on their cognate MHC to TCR as a first signal. This in turn allows for the second signal or the formation of an immunologic synapse made up of costimulation molecules traveling from the periphery of each cell to the point of contact. Once engaged the T cell undergoes a third signal kickstarting the cell cycle to activate proliferation. It is at the point of this synapse where recent studies have shown the migration and presence of mitochondria to "power" these interactions. In addition to location, mito shape also has a direct impact on the metabolic profile of T cells. For example, forcing mito fusion can skew an effector-type T cell utilizing anabolic metabolism to memory-like T cells dependent upon catabolic pathways. These changes in mito ultrastructure ultimately impact the function of T cells, and similar functional consequences have been described in dendritic cells (DC). Although, ECs are semi-professional APCs, nothing is known about how mito morphology affects EC immunogenicity, especially in the setting of Tx. The inventors set out to investigate the role that mito morphology has on the immunogenicity of ECs in organ Tx. The central premise is that modulation of mito morphology pre-Tx in the donor organ will improve post-Tx outcomes by blunting early responses to IRI by ECs and creating a "window" wherein subtherapeutic doses of immunosuppression can maintain long-term graft survival without the predisposition to harmful sequelae of these necessary drugs.

Certain Definitions

As referred to herein, M1 is the compound:

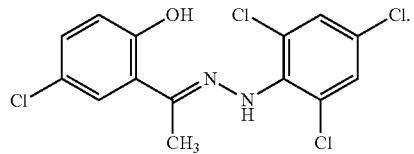 [SMILES: C/C(=N\Nc1c(Cl)cc(Cl)cc1Cl)c1cc(Cl)ccc1O]

As referred to herein, Mdivi1 is the compound:

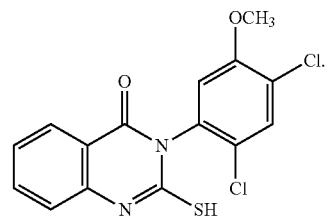 [SMILES: COc1cc(-n2c(S)nc3ccccc3c2=O)c(Cl)cc1Cl]

The term "therapeutically effective" refers to the amount of the composition used is of sufficient quantity to ameliorate one or more causes or symptoms of a disease, disorder or condition. Such amelioration only requires a reduction or alteration, not necessarily elimination. Preliminary data suggest a dosage of 40 µM of M1 and 20 µM of Mdivi1 will have effects on the microvascular endothelial cells.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

The term "treatment" refers to the medical management of a patient or an organ with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "prevent" or "suppress" refers to a treatment that forestalls or slows the onset of a disease or condition or reduced the severity of the disease or condition. Thus, if a treatment can treat a disease in a patient or an organ having symptoms of the disease, it can also prevent or suppress that disease in a patient or an organ which has yet to suffer some or all of the symptoms.

The term "inhibit" refers to a decrease in an activity, response, condition, disease, or other biological parameter. This can include but is not limited to the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

Formulation with Pre-Treatment Solution

The formulation of the invention to pre-treat an organ prior to transplantation includes a preservation solution. A skilled artisan would readily understand that any preservation solution currently in use can be used. Commonly used solutions include: University of Wisconsin (UW) solution, Belzer UW Cold Storage Solution, Viaspan, CoStorSol, Kyoto ET Solution, Celsior Solution, Phosphate Buffered Sucrose Solution, Bretschneider Histidine Tryptophan Ketoglutarate (HTK) Solution, Ross-Marshall Citrate Solution, Euro-Collins Solutions and Perferdex. Different solutions are used for different organs, such as Perfedex for the lung. In addition, different solutions are preferred at different institutions. In another embodiment, the formulation of the invention to pre-treat an organ prior to transplantation can be applied to a warm perfusate in normothermic machine perfusion. Non-limiting examples of warm perfusates that have been used in experimental models and trials include whole blood, blood-based mixtures enhanced with metabolites, Steen solution (XVIVO Perfusion Inc, Denver, Colo.), and a combination of fresh frozen plasma and packed red blood cells.

In one embodiment, University of Wisconsin (UW) solution, which was developed for liver, kidney, and pancreas preservations, can be used in the formulation of the present invention. UW solution is considered the standard for renal, pancreas, and hepatic preservation, effectively extending the ischemic time for kidneys, pancreas and livers and allowing them to be transported considerable distances to waiting recipients. The composition of the solution is complex. The solution has an osmolality of 320 mmol kg$^{-1}$ and pH 7.4 at room temperature and is composed of the following: Potassium 135 mmol L$^{-1}$, Sodium 35 mmol L$^{-1}$, Magnesium 5 mmol L$^{-1}$, Lactobionate 100 mmol L$^{-1}$, Phosphate 25 mmol L$^{-1}$, Sulphate 5 mmol L$^{-1}$, Raffinose 30 mmol L$^{-1}$, Adenosine 5 mmol L$^{-1}$, Allopurinol 1 mmol L$^{-1}$, Glutathione 3 mmol L$^{-1}$, Insulin 100 U L$^{-1}$, Dexamethasone 8 mg L$^{-1}$, Hydroxyethyl starch (HES) 50 g L$^{-1}$, and Bactrim 0.5 ml L$^{-1}$. The components of UW solution, as with the other aforementioned solutions, are utilized to prevent cellular edema, cell destruction, maintain organ metabolic potential, and to maximize organ function after perfusion is reestablished.

Additional Components of Formulation for Administration

The formulations can be used therapeutically in combination with a pharmaceutically acceptable carrier. Pharmaceutical carriers are known to those skilled in the art. These most typically would be standard carriers for administration of drugs to humans, including solutions such as sterile water, saline, and buffered solutions at physiological pH. Other compounds will be administered according to standard procedures used by those skilled in the art. Pharmaceutical compositions can include carriers, thickeners, diluents, buffers, preservatives, surface active agents and the like in addition to the molecule of choice. Pharmaceutical compositions can also include one or more active ingredients such as antimicrobial agents, anti-inflammatory agents, anesthetics, and the like.

Some of the compositions can be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

The invention will now be further described in the Examples below, which are intended as an illustration only and do not limit the scope of the invention.

EXAMPLES

Experimental Models: human umbilical vein endothelial cells (HUVECs, Lonza) will be used. At basal level MCEC and HUVEC mitochondria are small and rounded, with no evidence of elongation or fragmentation. To mechanistically dissect the impact of mito fission and fusion on the EC immune outcomes the inventors will utilize the following novel cell reagents: MCECs and HUVECs will be transfected with Mfn2 and $Drp1_{k38A}$ overexpression plasmids. Transfection will be confirmed by western blot and qPCR analysis. Effect on mito shape will be confirmed by mitotracker red and quantified The inventors will also utilize fusion promoter M1, which enhances the GTPase function of the fusion proteins Mfn1, Mfn2, and the fission inhibitor Mdivi-1, which inhibits self-assembly of the fission protein Drp-1, to force mito elongation in ECs. Use of genetic manipulation of fusion will ensure that in the co-culture studies that microenvironmental factors do not override fusion induction, which could potentially occur with the therapeutic compounds, M1/Mdivi-1.

Hypoxic cold storage and reperfusion injury culture model: A modified cell culture model that simulates the IR process of organ Tx will be used. Briefly, a confluent monolayer of MCECs will undergo a period of simulated cold ischemic time (CIT) for 6 hrs. by replacing the DMEM containing 10% FBS with UW or UW augmented with M1, Mdivi-1 or a combination of M1/Mdivi-1. Cells will then be sealed in a hypoxic chamber filled with nitrogen at 4° C. After CIT, cells will undergo simulated reperfusion by removing the preservation solution and reintroducing fresh DMEM containing 10% FBS.

Example 1

Forced Mito Fusion and Impact on EC Barrier Integrity

Trans-endothelial resistance (TEER): the inventors will assess the impact of mito shape on EC barrier function. Transfected ECs and pharmacological inhibitor treated ECs, will be grown to confluence in transwell culture conditions and exposed to CIT and barrier functions recorded. Given the associations between mito morphology and alteration of key GJ protein connexin 43 (Cx43), the inventors will determine Cx43 and zonula occludin-1 (ZO-1) expression levels by western blot and immunofluorescent staining. The inventors predict given the metabolic data that EC mito fusion will improve GJ and TJ expression and thus improve barrier functions. While TEER is used as a measure of barrier function, it does not specifically address barrier permeability. Therefore, barrier permeability will be measured by FITC-dextran studies as described. Finally, as control for these experiments. The inventors will assess the impact of mito morphological manipulations on cell injury. Fluorescein diacetate and propidium iodide (FDA-PI) viability staining will be used to determine the damage induced on these cells by CIT, and determine the extent to which mito fusion inhibits cell death. Importantly, the inventors have not seen any increased cell death associated with M1/Mdivi-1 therapy in any of the experimental studies (data not shown).

Example 2

Mito Morphology Impact on EC Adhesion and Co-Stimulatory Molecule Expression Adhesion/Co-stimulatory molecule expression: ECs control microvascular barrier function, innate immune cell adhesion, and prime recipient T cells post Tx, in part by adhesion molecule and immunological co-stimulatory molecules expression. The inventors will characterize surface molecules on MCECs and HUVECs at baseline and in the CIT injury model at 0, 6, 12, 18, 24 hrs post-reperfusion. Target molecules to be evaluated include MHC I, MHC II, costimulatory molecules (CD80, CD86), coinhibitory molecules (PD-L1, PD-L2), and adhesion molecules (P-sel, E-sel, ICAM-1, VCAM-1, and LFA-3), and will be analyzed by western blot and flow cytometry. The preliminary data with MCECs suggests that M1/MDivi-1 therapy, up regulates PD-L1.

Example 3

Mito Morphology Impact on T Cell Proliferation/Activation

Figure 2:
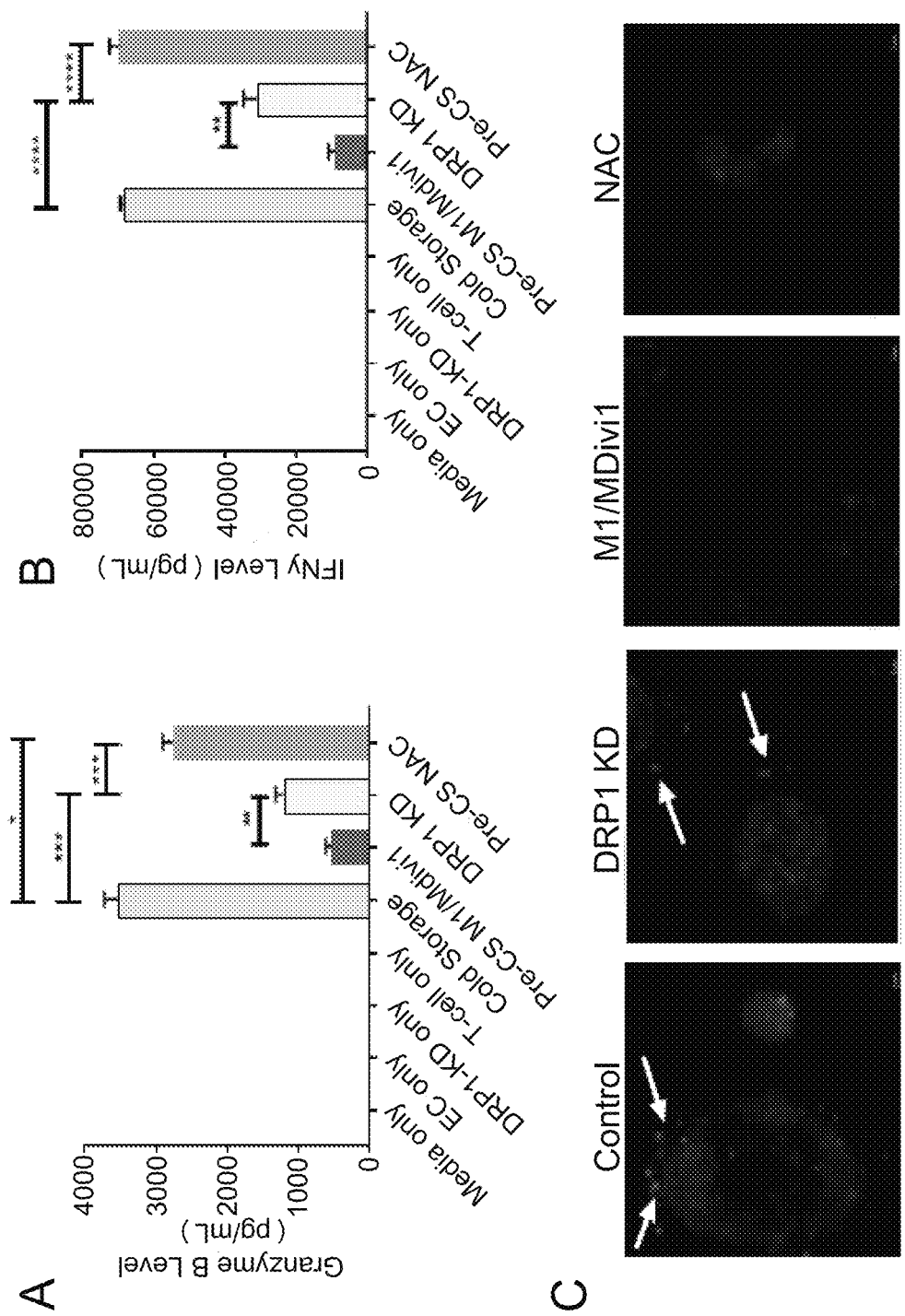
FIG. 2 shows M1/Mdivi-1 reduces alloreactive CD8 cytokine production and downregulates Mito ROS. (A and B). DRP1-KD and M1/Mdivi-1 reduce CD8 T cell production of Granzyme B and IFN-gamma, whereas NAC antioxidant therapy has no impact. (C). Analysis of mito ROS with mitoSox fluorescent probes demonstate that CIT induces ROS, that is reduced by DRP1-KD, and abrogated completely by M1/Mdivi-1 and NAC therapy, suggesting that T cell responses are independent of intracellular ROS effects.

EC/T cell co-culture: Using the genetically modified and pharmacological inhibitors the inventors will dissect the impact of EC mito morphology manipulation on T cell activation/co-stimulation. These studies will focus on MCECs given the availability of reagents and ability to generate alloreactive CD8 T cells as previously published. The inventors demonstrate that M1/MDivi-1 treatment suppresses alloreactive CD8 production of GrB and IFNγ, and that this appears in part to be modulated by the expression of PD-L1. While these data support a role for mito fusion in inducing T cell responses, recent data suggests that along with inhibiting Drp1, it may also reversibly inhibit mito complex 1 which may lead to a decrease in reactive oxygen species (ROS). To investigate this further, and to confirm the effects the inventors have shown are associated with mito fusion and not solely antioxidant properties, the inventors have utilized shRNA to stably knockdown DRP-1 (DRP1-KD) in the MCECs. The inventors demonstrate that Drp1-KD is associated with mito elongation that is in keeping with M1/MDivi-1 treatment, and that elongation persists even following CIT (FIG. 1). Drp1-KD not only exhibited elongated mitochondria and increased mito mass but was also able to dampen the functional activation of T cells shown by a significant decrease in GrB and IFNγ as compared to cold storage injured ECs, confirming the findings with M1/Mdivi1 pharmacotherapy (FIGS. 2A & B). In order to assess whether the anti-oxidant properties of Mdivi-1 contribute to the dampening of EC immunogenicity the inventors also compared a known anti-oxidant, N-Acetyl Cysteine (NAC,) which has undergone clinical trials to assess its effects on T cell activation in comparison to DRP1-KD EC and M1/Mdivi-1 treated EC. Both DRP1-KD and M1/Mdivi-1 cold stored and treated ECs significantly decrease the release of GrB and IFNγ by co-cultured CD8s in comparison to NAC, which had no significant effect (FIGS. 2A & B). The inventors next sought to determine if mito elongation via DRP-KD or M1/MDivi-1 impacted intracellular ROS in the model system. Using mitoSOX staining the inventors demonstrated that CIT is associated with significant mito ROS, that DRP1-KD reduced mito ROS, and that both M1/MDivi-1 and NAC completely abrogated ROS. Taken together, these data support the role of mito elongation in decreasing the immunogenicity of EC independent of the antioxidant properties, but further demonstrates that M1/Divi-1's superior effects in modulating T cells may be due in part to its antioxidant capacity.

Therefore, to build on these preliminary observations, the inventors will determine how mito EC modifications influence T cell proliferation, phenotype, and cytokine expression. Allogenic CD8 T cells will be generated. In brief, C57Bl/6 mice will be inoculated with MCECs i.p. and 3 weeks later spleens will be harvested and CD8 T cells isolated using bead isolation techniques. These MCEC alloreactive CD8 T cells will then be co-cultured with MCECs in the normoxic and CIT models.

T cell proliferation: To determine how mito morphology impacts the immunogenicity of ECs to alloreactive CD8 cells the inventors will label CD8 with CFSE and monitor proliferation at 24, 48, 72 hrs, and 4 and 7 days by standard techniques. The inventors anticipate, given the preliminary data, that mito fusion will significantly reduce T cell proliferation.

T cell phenotypes: Antigen presentation, through the expression of different co-stimulation and co-inhibitory signals promotes T cell proliferation and phenotypic differentiation. To more thoroughly dissect the impact of mito morphology on EC induced allogeneic CD8 responses the inventors will phenotypically characterize T cell surface markers at the timepoints listed above. Panels include: T cell subsets; T Effector $CD62L^-CCR7^-CD27^+IL-7R\alpha^{+/-}KLRG-1^{++}$, T late effectors $CD62L^-CCR7^-CD27^+IL-7R\alpha^-KLRG-1^{+++}$, central memory $CD62L^+CCR7^+CD45RO^+CD44^+CD2^{high}$, Tregs $CD8^+CD25^+FoxP3^+$.

Cytokine Secretion: Culture supernatants will be sampled at 24, 48, 72 hrs, and 4 and 7 days and assessed by FlexMap 3D multiplex panel cytokine analysis for IL-1β, IL-2, IL-4, IL-6, IL-10, IL-12, IL-13, IL-17, TNFα, IFNγ, GrB, IP-10, TGFβ, KC, and MIP-1α. The inventors acknowledge that this a complex list, but given the capabilities of the Flexmap system the inventors have opted to be inclusive, given that a large number of analytes can be measured simultaneously using low sample volumes.

Figure 3:
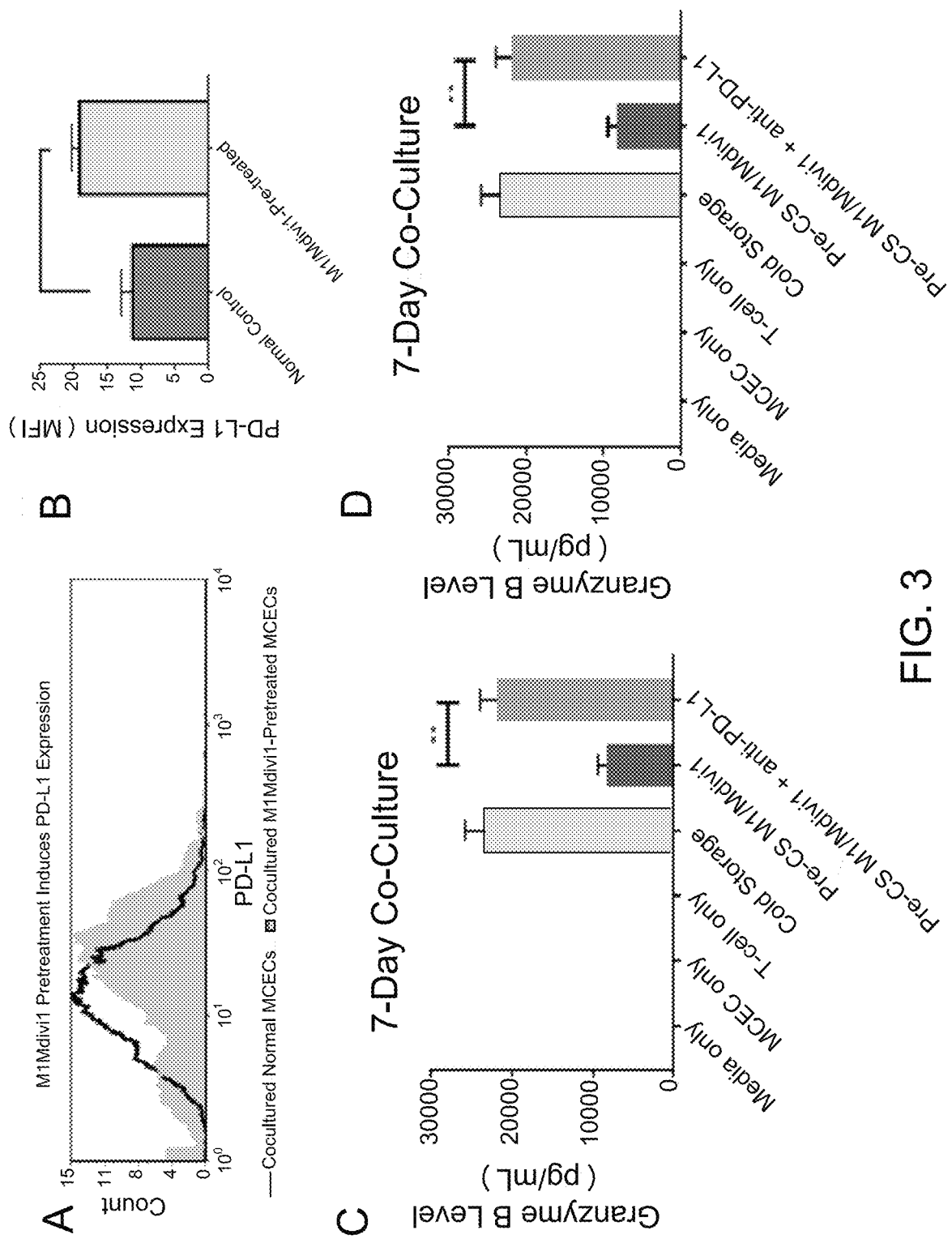
FIG. 3 shows M1/Mdivi-1 induces PD-L1 upregulation. (A and B). M1/Mdivi-1 pretreatment induces PD-L1 upregulation. (C and D). PD-L1 blockade breaks M1/Mdivi-1 associated control of T cell cytokine production.

EC surface molecule expression blockade: Alterations to EC mito morphology may induce a variety of changes to the EC that could induce the suppression of allogeneic CD8 responses the inventors detail herein. Alterations in adhesion and co-stimulatory molecule expression as a consequence of BD, IRI and transplantation have been shown to be key factors in modulating adaptive immune responses post-transplantation, and given the preliminary data, will be the focus the mechanistic studies on these surface molecules. The inventors will perform blocking antibody studies, using the data generated from the flow and western blot EC surface molecule expression studies, to drive the EC/T cell investigations. The inventors have already shown that M1/MDivi-1 treated cells up regulate PD-L1 and have further demonstrated that blockade of PD-L1 restores M1/MDivi-1 treated cells immunogenicity (FIG. 3). The inventors will utilize this same approach to dissect the impact of other surface molecules, identified in the screens, to determine their impact on CD8 responses. Blocking antibodies are available for all of the surface molecules the inventors propose to characterize. Ab dilutions will be determined based on manufactures recommendation and published literature. All will be administered at the time of reperfusion.

ECs are central to the injury process early post transplantation. They act as a physical barrier, promote cell transmigration, and prime adaptive immunity. Here the inventors study all of these factors and determine how mito influence these EC properties. To investigate barrier function the inventors propose to utilize TEER and permeability assays. The TEER data shows that M1/Mdivi-1 therapy during CIT facilitates quicker recovery from injury. The mechanisms accounting for this are currently unclear. The inventors hypothesize that mito fusion will improve tethering of Cx43 and ZO-1 and the inventors plan to explore this in confocal co-localization studies. The inventors do not anticipate any issues with the experimental methodology given the preliminary studies and the prior experience with these model systems. The inventors anticipate that promoting mito fusion will reduce the ability of ECs to stimulate T cell activation by decreasing the expression of costimulatory molecules and increasing the expression of coinhibitory molecules on their surface. In addition, and given the preliminary data, the inventors would expect that costimulation and pro-inflammatory adhesion molecule expression to be significantly reduced in the CIT model in DRP1-KD, Mfn, $DRP1_{k38A}$, and M1/Mdivi-1 treated cells. A potential challenge is if the genetically altered cells inhibit ROS suggesting the antioxidant property of inhibiting DRP-1 as a mechanism of action. The preliminary data show that in DRP-KD cells inhibition of T cell activation is independent of antioxidant characteristics as NAC treated cells do not decrease Granzyme-B to the extent of DRP-KD. Therefore, the inventors anticipate this to be the case in Mfn, $DRP1_{k38A}$, and M1/Mdivi-1 treated cells. The inventors will employ a similar strategy to compare NAC to the other constructs. Additionally, the inventors will employ the use of mitoSox to dissect the influence of ROS on injury on treated ECs. The inventors may also see a difference between HUVEC and MCEC however these data will contribute a greater understanding of the mechanism of protection which would be clinically useful.

Example 4

Impact of Mito Forced Fusion on Immune Synapse Interactions and T Cell Activation During T-cell and APC interaction, an immune synapse is formed to facilitate signaling efficiency important for T-cell activation. During this process, mitochondria translocate to the peripheral supramolecular activation cluster (pSMAC) of the immune synapse to provide energy to ATP-consuming processes and to maintain calcium flux. Baixauli et al., have demonstrated that the fission protein DRP-1 is required for mito positioning and localization at the pSMAC in T-cells. Mito translocation to immune synapses has also been observed in other cells, including NK cells and B-cells. In fact, during antigen presentation, B-cell's orient their microtubule-organizing center, Golgi apparatus, and WIC II$^+$ vesicles toward the synapse, and additional evidence indicates that mitochondria are also localized to the synapse in the APC to provide energy and maintain calcium flux. For mitochondria to efficiently translocate, they need to move as small organelles instead of as a network, and the fusion protein Mfn2 can make mitochondria become stationary by tethering them to the endoplasmic-reticulum. Based on these observations, the inventors hypothesize that in ECs, forcing fusion will impair mito translocation to the immune synapse between EC and T-cell, thus impairing antigen-presentation.

The inventors will again utilize ECs and pharmacologic reagents (M1 and Mdivi-1) listed in sub-aim 1.1., but in this aim focus the immunological studies on mouse cells to better characterize the immune interactions. The inventors will culture ECs in normoxic or under CIT conditions and co-culture these ECs with allogeneic sensitized CD8 T cells, generated as the inventors have previously described. In brief, the inventors will inoculate C57B/6 mice with MCECs from FVB strain. Three weeks later, the inventors will isolate spleens and purify CD8+ T cells by Macs bead isolation. The inventors have shown that this method generates T cells allogeneic to MCECs. Six, 24 and 48 hrs after initiation of cocultures, the inventors will analyze EC-T-cell complexes. Cell complexes will be fixed and stained for CD31 and CD8 to visualize the plasma membranes of MCECs and T-cells, respectively, and for TOM20 to visualize the mitochondria using a super-resolution confocal microscopy. In a parallel set of experimental groups, the inventors will stain the cell complex for CD31, CD8, Mfn2 and calreticulin (an endoplasmic-reticulum (ER) marker) to visualize the co-localization between mitochondria and ER to determine whether mitochondria are tethered to the ER under forced fusion. The inventors will also stain the cell complex for CD31, CD8, cytoskeleton actin, and DRP-1 to determine whether mitochondria are tethered to the cytoskeleton near the immune synapse. Lastly, the inventors will perform functional co-culture assays to determine the direct impact of EC mito morphology on T cell activation. T-cells will be co-cultured with normoxic normal EC or CIT injured EC. Groups will again be shDRP1-KD, Mfn2, $DRP1_{k38A}$, and M1/Mdivi-1 treated cells.

Figure 4:
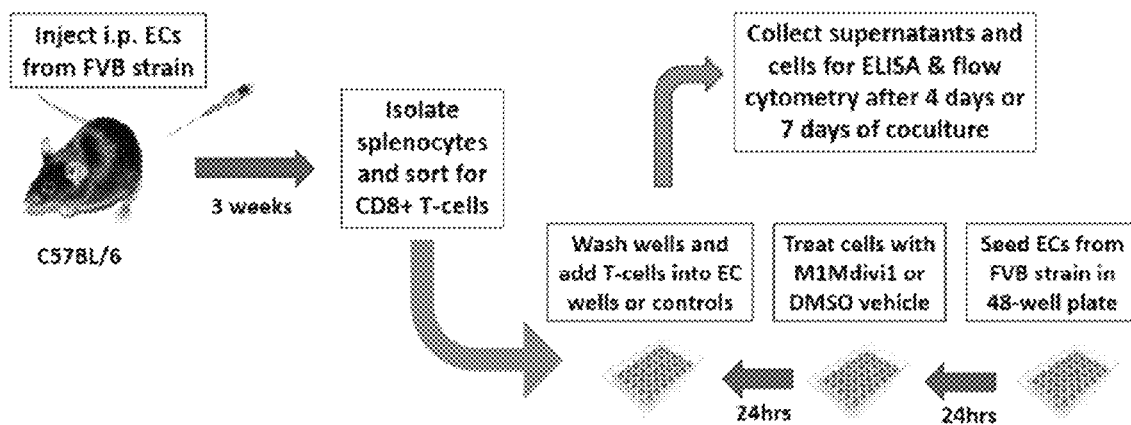
FIG. 4 shows M1/Mdivi-1 pretreatment of MCECs prior to co-incubation with allogeneic CD8+ T cells result in reduced Granzyme B (A) and IFN-gamma (B) production after 7 days.
Figure 4:
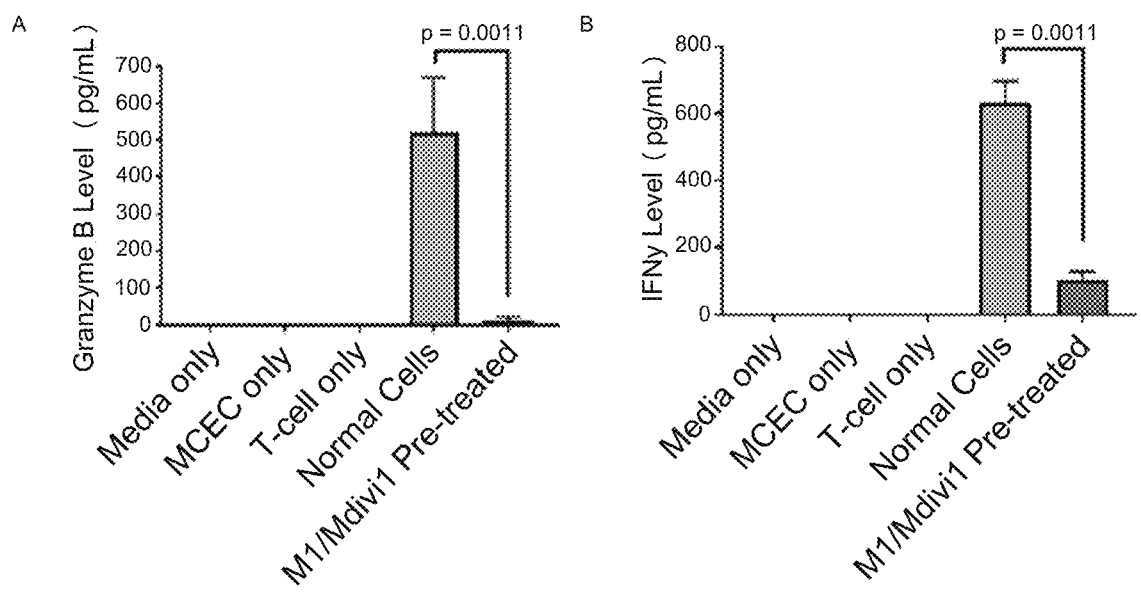

The inventors anticipate that forcing mito fusion will alter the morphology into tubular structures that will impair mito trafficking and inhibit immune synapse formation. The result of which is likely to reduce T cell proliferation, effector function, and decrease T cell effector molecule release. Mfn2 plays important roles in tethering of mitochondria to the ER and, thus, the inventors anticipate in cells overexpressing Mfn2 that very little synapse activity will be determined. In terms of T cell outcomes, the inventors have shown that co-culture of T cells in ECs pretreated with M1/Mdivi-1 reduces T cell effector molecule release (FIG. 4), whether the inventors will see a different T cell phenotype is difficult to predict. Preliminary data suggests that regardless, T cell activation is impaired when DRP-1 is inhibited in the EC; therefore, if mito trafficking is not altered these data would still be of significance given that the functional outcome is altered, suggesting a mechanism independent of trafficking in the EC which would be a novel finding in and of itself. The inventors do not anticipate any problems with the proposed aim.

The inventors anticipate forced mito fusion in several in vitro models to impair the ability of EC to activate memory-like CD8$^+$ T cells which are spared by conventional induction immunosuppression, and lead to early rejection responses worsened by IRI. The inventors anticipate the mechanism of this impairment lies in the ability of M1/MDivi-1 to efficiently dampen costimulation, upregulate coinhibitory molecules, and possibly affect mito trafficking and immune synapse formation. Thus, treatment of EC prior to the formation of an immunologic synapse with effector T cells (i.e. pretreatment) is feasible and translatable method of conditioning allografts prior to Tx as ECs are isolated in the organ during the preservation phase. The inventors acknowledge that mito morphology may affect many systems, such as TLRs, inflammasomes, and ROS. However, here the inventors have sought to focus specifically on EC surface marker expression and how this impacts the EC/T axis post-Tx, so as to be focused mechanistically and so that the application doesn't appear overly ambitious.

Example 5

Figure 5:
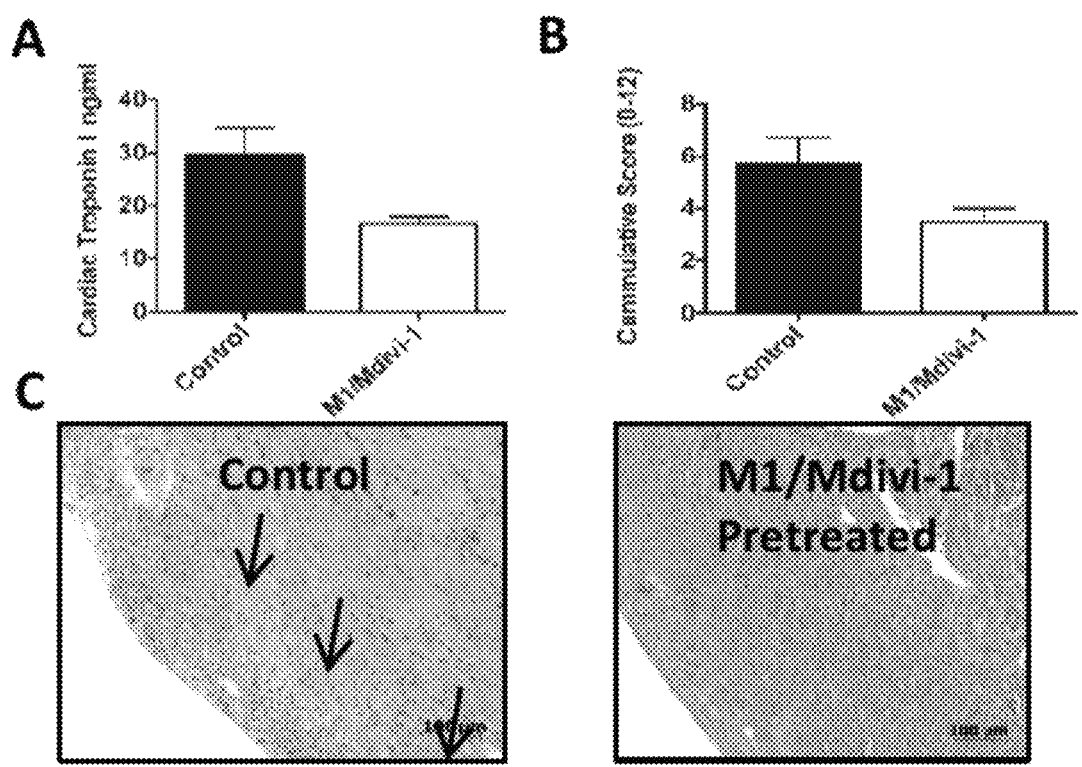
FIG. 5 shows recipient treatment with M1/Mdivi-1 reduces IRI. (A). Serum cardiac troponin I levels are reduced in treated recipients. (B). Quantification of histological injury shows a marked reduction in histologically detectable injury. (C). Representative H&E images of cardiac injury and inflammation, note the increased epicardial injury in control untreated hearts 24 hrs post-Tx (arrows).

Impact of Mitochondrial Morphology on Ischemia Reperfusion Injury (IRI) and Acute Transplant Rejection (AR) In Vivo Alterations in mito morphology alters cell/organ susceptibility to IRI. Previous studies investigating focal myocardial ischemia have shown that induction of mito fission post IR results in cell death, loss of endothelial barrier function, and the induction of pro-inflammatory adhesion molecules, whereas, promotion of mito fusion results in an IR protective phenotype. The mechanisms associated with protection are thought to be multifactorial, and are incompletely elucidated. Available data suggests that mito fusion reduces cellular injury and improves GJ stability; thus, improving microvascular EC barrier function, and the preliminary in vitro data supports a role for altered EC-T cell priming. To build upon these observations, the inventors performed preliminary experiments in the rodent model of Tx. C57Bl/6 donor hearts were transplanted into Balb/c recipients. Upon reperfusion, recipients received a dose of 2.4 mg/kg M1, and 1.2 mg/kg Mdivi-1 determined by published studies utilizing the same doses in vivo. Recipient treatment of M1/Mdivi-1 led to reduced cardiac troponin I levels and reduced evidence of histological myocyte injury and inflammation in the Tx heart (FIG. 5). These data provide 'proof of principle' for the approach to modify mito morphology as a means to improve post-Tx outcomes. Given previous studies, and the preliminary data, the inventors will target the studies on three key components of post-Tx outcomes: IM, early allogeneic CD8 T cell infiltration, and acute rejection (AR). The inventors will mechanistically focus on EC activation, EC-T cell interactions, and EC barrier function. The inventors will utilize established models of mouse cardiac transplantation together with a clinically relevant rodent brain death (BD) model. The inventors will also assess the ability to manipulate mito ultrastructure in the setting of both hypothermic and normothermic preservation.

The studies proposed will delineate the role of mito morphology alterations in cardiac-Tx. They will also determine how donor BD impacts IM, and identify an optimum drug delivery strategy for reducing acute post-Tx injury through mito shape manipulation. The opposing roles of mito fission and fusion regulate mito morphology and function. A number of key proteins have been identified which control this process (DRP-1, mito fission protein-1 (Fis-1) and mito fission factor (mff), Mfn1/2, and OPA-1). Given the importance of these proteins for the maintenance of cellular respiration, genetic deletion is most often fatal. However, C57Bl/6 homozygous mito fission factor (Mff)-deficient (Mff$^{gt}$−/−) mice are available, as are pharmacological promoters of fusion, M1 and Mdivi-1. Mdivi-1 has previously been shown to promote cardioprotective effects in rodent models of focal cardiac ischemia, and the inventors have shown that M1/Mdivi-1 provides protection from allograft IRI (FIG. 5), when administered pre-injury in a large bolus. Importantly, systemic administration of Mdivi-1 had no detectable adverse side effects. In vitro data shows M1/Mdivi-1 can alter mito morphology under both normoxic and cold hypoxic (FIG. 1) conditions. Using these tools, the inventors will dissect the role of fission and fusion in IRI and rejection in the context of organ Tx. The inventors propose three sub Aims. In SA 2.1, the inventors will determine the impact of mito fission inhibition, and thus fusion promotion, through comparing the effects of IRI and AR of recipients receiving hearts from C57Bl/6 wildtype (wt) or C57Bl/6 homozygous mito fission factor (Mff)-deficient (Mff$^{gt}$−/−) donors. In SA 2.2 the inventors will explore the therapeutic potential of donor heart pre-treatment with M1, Mdivi-1, and a combination of both. In SA 2.3, the inventors will explore the application of subtherapeutic immunosuppressive regimens. Immunosuppression, while necessary, carries serious side effects that limit the survival of patients with solid organ Txs, and therefore strategies that can reduce this burden are urgently needed, and will be explored. The inventors will explore the cardioprotective efficacy of these agents administered to either the donor or as constituents of the donor organ preservation solution, or under normothermic conditions using the novel BD model.

The inventors will investigate the impact of mito morphological changes on post-Tx IRI using the abdominal heterotopic heart allograft model. To investigate the impact of mito morphology change on IRI the inventors will utilize donor animals deficient in mff. C57Bl/6 Mff$^{gt}$−/− (Fusion promoter), and C57Bl/6 wildtype, donor hearts will be stored in UW solution for 6 hrs prior to Tx into Balb/c recipients.

Experimental procedures: For allograft IRI, hearts and serum will be isolated 12 and 48 hrs post-Tx, as the inventors and others have shown that these are peak time points for neutrophil and memory CD8 T cell infiltration. Balb/c-C57Bl/6 living donor allograft pairing leads to AR with complete rejection and cessation of beating at 7±2 days post-Tx. To determine the impact of mito fusion on AR, the inventors will harvest allografts at 7 days to determine differences in immune cell infiltrates, and will analyze graft rejection by performing graft survival studies. Graft failure will be determined by manual palpation as described, and confirmed by visual inspection. Portions of the grafts from IRI and AR studies will be frozen, preserved for paraffin processing, stored for electron microscopy, and disaggregated for flow cytometry.

Fusion Promotion Ameliorating Cardiac Allograft Post-Tx IRI

Histopathology: H&E stain will be used to assess histopathological evidence of damage as described. Morphological changes in intravascular red blood cells will be determined (parachute, arrow, swallow, massed) as markers of stopped, turbulent, or blockage of microvascular flow, as described. For biochemical readouts, pre- and post-Tx serum will be collected and cardiac troponin I and LDH measured.

Cold Storage and IRI Impact Mito Shape of EC and Cardiomyocytes

Mito morphology will be analyzed at five time points; 1. Harvest, 2. After 6 hr UW cold storage, 3. 12 hrs post Tx, 4. 48 hrs post Tx, and 5. 7 dys post Tx. Mitochondria structure will be assessed by electron microscopy of samples fixed in 2% glutaraldehyde in 0.1 mol/l sodium cacodylate buffer, and post-fixed in 1% osmium tetroxide. Samples will be visualized using a Hitachi H600 electron microscope (histology core facility). At least 30 cells in 5 randomly selected fields will be observed and mitochondria structure, shape and distribution determined in myocytes and ECs by observers blinded to the experimental group.

Mito Fusion Impact on Endothelial Barrier Function, EC Activation and Cytokine Expression Evans Blue (EB) Barrier Permeability Assays: Mito fusion has been shown to promote GJ stabilization by preventing the degradation of connexin43, a key GJ constitute. To assess how altered fission/fusion impacts EC barrier function the inventors will perform in vivo EB studies. EB uptake will be quantitated by biochemical and histochemical assays as described at 6 and 48 hrs post Tx. To assess GJ and tight junction protein turnover the inventors will stain heart sections with mouse anti-ZO-1 antibody and anti-Connexin 43 and visualize with Alexa 488/555 secondary antibodies. Staining will be quantified by Confocal Microscopy and MetaFluor image analysis software. Quantification of GJ proteins will also be assessed by western blot.

Adhesion molecule expression and leukocyte sequestration: The induction of adhesion molecules is an important mechanism by which microvasculature promotes injury, microvascular thrombosis, T cell adhesion, and IRI. The inventors will investigate expression of adhesion molecules and thrombosis by quantifying P-selectin, E-selectin, ICAM-1, LFA-3, and VCAM-1 by Western blot homogenized allografts and by IF microscopy.

Fusion Reducing EC Activation and Cytokine Expression

Cytokines/chemokines: The inventors will investigate how mito morphological states affect local (graft) and systemic expression of cytokines. A number of cytokines/chemokines are produced following IRI and are thought to be important in its pathogenesis. Cytokines reported to play a role in injury following IRI of solid organs (either promoting or limiting injury) include IL-1$\beta$, IL-2, IL-4 IL-6, IL-10, IL-12, IL-13, TNF$\alpha$, IFN$\gamma$, IP-10 TGF, KC, MIP-1, Mig, and the inventors will focus on these molecules here. The FlexMap 3D system will be used for analysis. The inventors acknowledge that this a complex list, but given the capabilities of the Flexmap system the inventors have opted to be inclusive, given that a large number of analytes can be measured simultaneously.

Fusion Reducing T cell Activation, Priming and Proliferation of Memory T Cells

Immune cell infiltration and EC activation: Heart grafts will be dissociated using the Milltenyi Biotec gentleMACS™ and Octo Dissociator as per the Miltenyi protocol. The inventors will also harvest spleen samples for T cell analysis. Samples will be analyzed by flow for T cell subsets; Tregs (CD4+CD25+FoxP3+CD127low), Teffs (Effector CD62L−CCR7−CD27+IL-7R$\alpha$+/−KLRG-1++, late effector CD62L−CCR7−CD27+IL-7R$\alpha$−KLRG-1+++, and central memory CD62L+CCR7+CD45RO+CD44+CD2high). EC activation markers; CD86/80, MHCI/II, PD-L1/L2, OX40, CD40. The inventors anticipate that skewing of mito towards a fused elongated state will result in reduced immune cell infiltration, and the inventors predict that EC co-stimulatory molecule expression will be reduced.

Example 6

Memory Cell Proliferation

To determine the impact of altered EC mito morphology on memory T cell graft infiltration and proliferation, the inventors will perform specific T cell sensitization experiments. Balb/c Thy1.1$^+$ mice will be sensitized with B6 splenocytes. Two weeks later, spleens will be isolated from these Balb/c Thy1.1$^+$ mice, from which CD8$^+$ T-cells will be isolated and inoculated into Balb/c Thy1.2$^+$ mice. 72 hrs later, Thy1.2$^+$ BALB/c inoculated mice will receive cardiac grafts from either C57BL/6 WT or C57BL/6 Mff−/−, or M1/Mdivi-1 treated donor hearts. Heart allografts will be harvested at 2 and 7 days post-Tx, and T cells isolated. The frequency of Thy1.1$^+$ and Thy1.2$^+$ heart infiltrating T-cells will be assessed by flow cytometry to determine the impact of mito fusion on specific memory T cell (Thy1.1$^+$ CD8$^+$) versus non-specific (Thy1.2$^+$ CD8$^+$) intra-graft infiltration, and will further be phenotyped using the panels outlined above.

Example 7

Global Cardiac IRI

The inventors will explore the application of fusion promoter (M1) and fission inhibitor (Mdivi-1) directly to the donor organ, prior to Tx. Using M1, Mdivi-1 or a combination of M1/Mdivi-1, the inventors hypothesize that treatment of the donor organ prior to implantation, under normothermic or hypothermic conditions will significantly improve post-Tx outcomes. There is currently a great interest in the use of ex-vivo organ perfusion systems, and most work is aimed at improving 'marginal donor'. Therefore in this application the inventors will utilize the novel mouse model of BD which the inventors have shown, exacerbates IRI and accelerates the onset of AR, and has a phenotype in keeping with clinically used donor organs.

Figure 6:
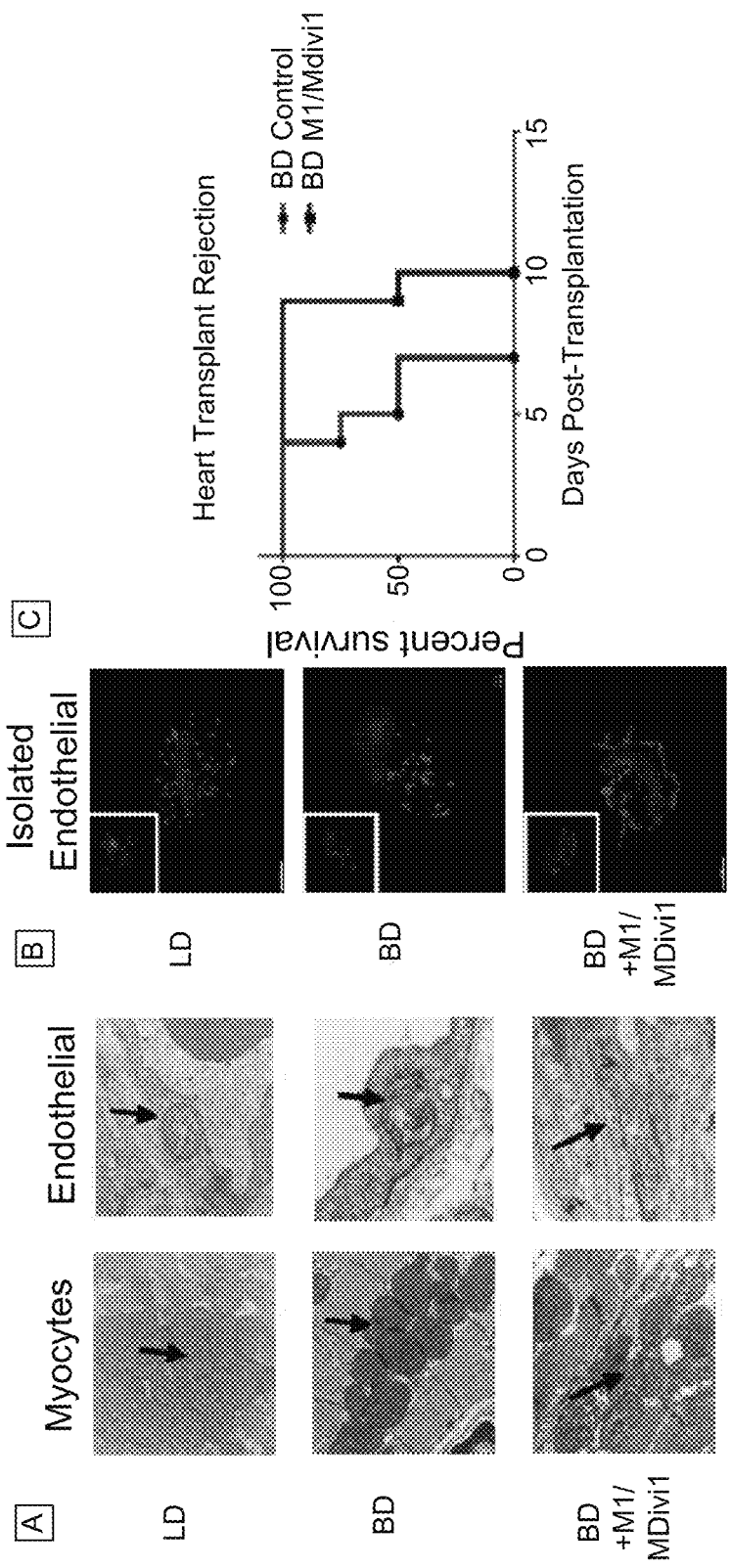
FIG. 6 shows M1/Mdivi-1 administered to the BD donor selectively elongates EC mitochondria and prolongs graft survival post transplantation. (A). Electron micrographs representative of 15 cells/expt n=2 demonstate elongation specifically of EC mito. (B). Confocal microscopy of ECs isolated from living donor (LD), brain dead (BD), BD+M1/MDivi-1 demonstrates clear elongation of EC mito. Images representative 15 cells/expt. n=3. (C). M1/MDivi-1 delivered to the BD donor prior to cardiac graft harvest results in a significant increase in graft survival. Single cell 3D reconstructions of mitotracker red of microvascular cardiac ECs.

Experimental design: The inventors will utilize the clinically relevant mouse model of BD as previously described. Using this model, the inventors will test the impact of M1, Mdivi-1 or a combination, in two therapeutic paradigms. 1. Augmentation of UW solution, under hypothermic conditions, and 2. Donor delivery under normothermic conditions. Graft survival will be monitored by daily manual palpation. As preliminary data to show feasibility and proof-of-principle, the inventors administered 2.4 mg/kg M1, and 1.2 mg/kg Mdivi-1 to C57Bl/6 brain dead donor mice prior to procurement of the hearts. The in vivo administration of M1/MDivi-1 resulted in site-specific mito elongation in the cardiac endothelium as electron micrographs of treated hearts revealed no mito elongation in the cardiac myocytes of treated donors (FIG. 6A). To further characterize these effects, the inventors isolated ECs from living donor, untreated BD and M1/MDivi-1 treated donors using miltenyi CD31 bead isolation techniques and qualitatively and quantitatively assessed mito elongation by confocal microscopy. The inventors demonstrated that M1/MDivi-1 treatment led to effective elongation of BD graft microvascular ECs (FIG. 6B). These "treated" hearts were then transplanted into allogeneic Balb/c recipients and compared against untreated BD wild type controls. Mito elongation significantly improved survival of the transplanted hearts when compared to controls; however, not indefinitely. Taken together, these results suggest that pre-conditioning of mito, specifically in the EC of target organs, plays an important role in the early survival of the graft (FIG. 6).

Models: 1. Augmentation of UW solution, under hypothermic conditions: Donor BD will be induced in C57Bl/6 mice and after 3 hrs of BD donor support, donor hearts will be harvested using a clinically relevant procurement protocol whereby following ligation of the superior and inferior vena cava, the inventors will clamp the thoracic aorta. The donor heart will then be isolated and perfused with 0.5 mL ice cold UW, or UW augmented with M1, Mdivi-1 or a combination of M1/Mdivi-1, via the proximal aortic arch, and all cardiac grafts stored for a period of 6 hrs in UW solution prior to Tx. For comparison, living donors will also be used, and graft procured and treated as above.

2. Donor delivery under normothermic conditions: Here the inventors will utilize the novel mouse model of BD to deliver M1, Mdivi-1 or a combination of M1/Mdivi-1 systemically through the carotid catheter under normothermic conditions, as a means to model ex vivo normothermic perfusion. The inventors will administer M1, Mdivi-1 or a combination of both 30 mins prior to donor heart harvest. The donor heart will then be isolated and perfused as described above, but this time no additional M1 or Mdivi-1 will be added to UW solution. Again, for comparison LD will also be used to dissect LD vs BD wherein LD donors will be perfused via the carotid as with the BD.

3. Therapeutic dose M1 and Mdivi-1: Based on preliminary (FIGS. 5 and 6) and published studies the inventors will administer 2.4 mg/kg M1 and 1.2 mg/kg Mdivi-1 or a combination of both at those doses. The inventors suggest a single dosing range based on the data and to minimize the experimental matrix such as it is not overly ambitious. Nevertheless, should the inventors determine no efficacy, the inventors will perform a dose escalation study.

4. EC Surface blocking antibodies: The preliminary findings suggest that alterations in EC surface molecule expression of adhesion, co-stimulatory and co-inhibitory molecules are affected by fusion of EC mito. To further dissect the mechanistic significance of these findings in vivo the inventors will employ blocking antibody strategies to determine the significance of these in vitro findings. The preliminary data supports a role for PD-L1 upregulation as a means to inducing EC dependent modulation of allogeneic CD8 T cells (FIG. 3). Given these findings, in this sub-analysis the inventors will utilize the in vivo model of Balb/c BD donors treated with the most effective dose, and therapeutic combination identified above and perform heterotopic cardiac Txs into C57Bl/6 mice. Recipients of pre-treated or control hearts will be administered anti-PD-L1 blocking Abs to determine whether the improved survival demonstrated in FIG. 6 is associated with an in vivo upregulation of PD-L1. Blocking PD-L1 will be administered at a dose and frequency as previously described. The inventors anticipate that administration of anti-PD-L1 Ab will break the prolongation of graft survival demonstrated in FIG. 6. The inventors acknowledge that other surface markers induced by mito fusion may play a role in this prolongation of survival. Should the in vitro studies identify other EC surface factors, they will similarly be explored using the same rationale as outlined for PD-L1.

Experimental Endpoints: Heart and serum will be isolated 12 & 48 hrs post-Tx for IRI and memory T cell functional studies as in SA 2.1, and survival determined as described above. All analyses outlined in sub-aim 2.1 will be performed in this sub-aim. The inventors will additionally analyze mito morphology by EM and confocal as described above in hearts procured after BD. The inventors will analyze mito morphology in a sub-group of hearts at the end of BD in M1/Mdivi-1 treated and untreated hearts, and after 6 hrs of cold storage with and without M1/Mdivi-1 augmentation of UW solutions. These studies will provide information regarding drug delivery and function, guide the dosing strategies, and further provide information on the impact of BD on mito morphology and injury.

The inventors have proposed an inclusive matrix of outcome readings to determine whether alteration of mito shape, with a focus on fusion, leads to protection from IR and AR. Although the experiments proposed at first glance appear as a list, these have been selected to determine key questions raised in Aim.1. The inventors will study 4 main components, 1. EC barrier function, 2. EC activation, 3. EC-T cell interactions and 4. Normothermic vs hypothermic drug delivery. Endothelial mito fusion and its impact on IRI and more specifically T cell interactions have not been studied previously. In this sub-aim the inventors utilize the only available genetic model to determine if forced fusion impacts post-tx outcomes. The inventors predict that fusion will promote reduction in IRI and given that the severity of IRI, and the development of AR are linked, the inventors suggest that the tempo and severity of rejection will be decreased. The inventors propose that these features will be induced by effecting the mito form in ECs, but acknowledge that changes in myocyte mitochondria will likely contribute to reduced injury, and thus reduced alloimmune responses. To more accurately study EC specific effects an alternative approach could be to develop an EC Mff conditional knockout to dissect the contribution of EC vs myocyte. The inventors have explored this possibility and have an NIH funded mouse knockout core at the facility and will employ this approach should the studies in the full deficiency prove difficult to complete. As an alternative, but also as a means to explore therapeutic translation of the findings the inventors have opted to use M1 and Mdivi-1 pharmacological modulation of mito fusion. Previous studies have shown that Mdivi-1 provides protection from IRI in cardiac focal ischemia model and the own preliminary data (FIGS. 5 & 6) shows proof of concept for the therapeutic potential. The inventors envisage that these reagents applied to the donor organ (normothermic and hypothermic, given the in vitro studies (FIG. 1) will result in mito shape change. Should the inventors find this not to be the case, the inventors will increase incubation time and drug doses. The inventors do not anticipate problems with being able to demonstrate/promote fusion given previously published in vivo studies, and as the inventors have shown in vivo efficacy (FIGS. 5 & 6). One potential delivery challenge is whether ex vivo addition of M1/Mdivi-1 at 4° C. will enable effective fusion. The inventors have shown that this is possible in vitro but have not demonstrated this in vivo. However, to counter this potential challenge the inventors have included a normothermic arm to the research and provide data that in vivo delivery of M1/MDivi-1 promotes EC mito fusion (FIG. 6). The inventors have opted to add the drug at 30 mins prior to graft harvest as the inventors do not want the drug to adversely impact the donor BD state. Should the inventors find that 30 mins is insufficient the inventors would add these drugs at earlier time points post BD induction. Fusion is associated with improved GJ stability, which can have multiple effects on IRI. Improved cell-cell communication, decreased EC activation and barrier function, leads to reduced immune cell adhesion and infiltration. If M1/Mdivi-1 forced fusion promotes this the inventors would anticipate unchanged Cx43/ZO-1 expression as compared to control, reduced EB uptake, adhesion molecule expression and innate immune cell infiltration. The inventors propose that mito fusion impairs immune synapse function and have proposed detailed in-vitro experiments to study this in aim 1. Here the inclusion of EC-memory T cell experiments has been proposed to determine whether EC-T cell axis is impacted in-vivo. The use of flow cytometry and adoptive Thy1.1 and 1.2 T cells will enable us to determine if treatment interferes with T cell phenotype, proliferation and function. The inventors anticipate that M1/Mdivi-1 will alter the immune synaptic capacity of the ECs and also lead to reduced co-stimulatory molecule expression, both of which will lead to reduced T cell proliferation/function. The inventors anticipate that AR will still occur in the donor treated hearts post-Tx but propose that inhibition of IRI and blockade of memory T cells activities will slow the tempo of rejection. $CD8^+$ alloreactive T cells are unresponsive to standard immunosuppressants and thus blockade of their proliferation will likely improve graft outcomes. The experiments proposed will enable us to mechanistically assess the potential for mito fusion promoting therapeutics in organ Tx. The inventors do not anticipate any difficulties with the methods. The inventors have 3 microsurgeons who complete 4/5 heart Tx/day and thus the experiments are feasible.

Example 8

EC Graft Mito Fusion and Immunosuppressive Sparing Regimens

Subtherapeutic Immunosuppression: The preliminary data revealed an improvement in cardiac Tx survival with single dose M1/Mdivi-1 in BD donors (FIG. 6) without long-term sustained survival. Thus, the inventors will utilize this "window" of early graft acceptance to administer subtherapeutic doses of immunosuppression to achieve the application of immunosuppressive sparing regimes. Previously the inventors have shown that subtherapeutic doses of Rapamycin can be administered together with subtherapeutic doses of regulatory T cell therapy to abrogate allograft vasculopathy. Using similar principles, the inventors will administer subtherapeutic doses of rapamycin to recipients of M1/Mdivi-1 hearts either in vivo or ex vivo and analyze graft survival by manual palpation. Groups will consist of: 1) BD donor into untreated C57Bl/6 recipients; 2) BD donor with M1/M-divi1 into untreated C57Bl/6 recipient; 3) BD donor into C57Bl/6 recipient treated with subtherapeutic rapamycin; and 4) BD donor with M1/M-divi1 into C57Bl/6 recipient treated with subtherapeutic rapamycin. Rapamycin will be administered as described previously. The inventors have shown that using this dose heart allograft survival is not significantly increased, and thus anticipate the inclusion of M1/MDivi-1 donor therapy will substantially improve survival. These groups will also be repeated utilizing LD.

Example 9

General Procedure

Figure 7:
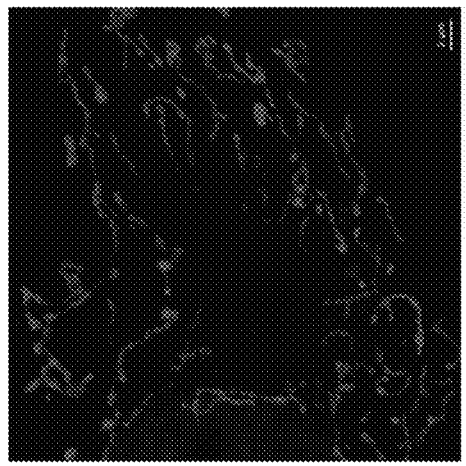
FIG. 7 shows that M1/Mdivi1 treatment of microvascular cardiac endothelial cells (MCECs) significantly elongates mitochondria.
Figure 7:
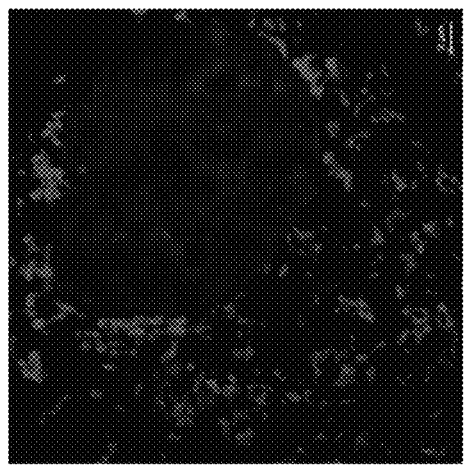
Figure 7:
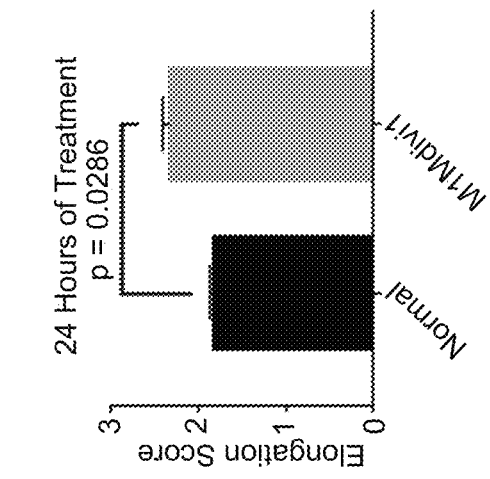
Figure 7:
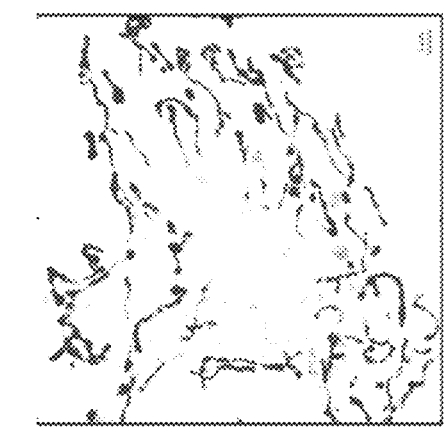
Figure 7:
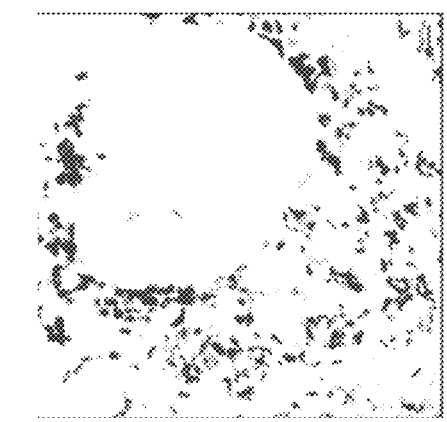

Utilized were microvascular cardiac endothelial cells (MCECs) and M1 (a fusion promoter), Mdivi1 (a fission inhibitor), in in-vitro models described below:
Validation of M1/Mdivi1 effects: seeded ECs→treated cells for 24 hours with M1/Mdivi1→stained with Mitotracker Red and DAPI blue→imaged with the confocal microscope Zeiss LSM 880;
Assessment of adhesion molecule expression: seeded ECs→treated cells for 24 hours with M1/Mdivi1→activated cells for 24 hours with TNFα/IFNγ→flow cytometry; and
Coculture: seeded ECs→treated cells for 24 hours with M1/Mdivi1→cocultured ECs with sensitized allogeneic CD8+ T-cells for 7 days→ELISA and flow cytometry.
As shown in FIG. 7, MCECs were treated with 40 µM/20 µM M1/Mdivi1 for 24 hours prior to staining with Mitotracker Red and DAPI (blue), and imaging with Zeiss LSM 880 confocal microscope equipped with Airyscan. (A) Confocal images demonstrated pronounced elongation of MCEC mitochondria in M1/Mdivi1 compared to normal controls, which was confirmed by morphological quantification using ImageJ analysis (B). Images are representative of 3 independent experiments with 5 fields taken per experiment. Mann-Whitney test was applied, p=0.0286. Scale bars are 2 µm.

Example 10

Figure 8:
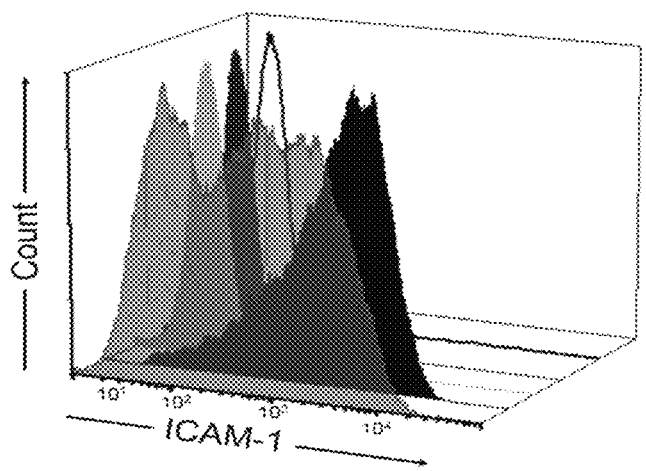
FIG. 8 shows that pretreatment of activated microvascular cardiac endothelial cells with M1/Mdivi1 results in decreased expression of endothelial cell adhesion molecules.
Figure 8:
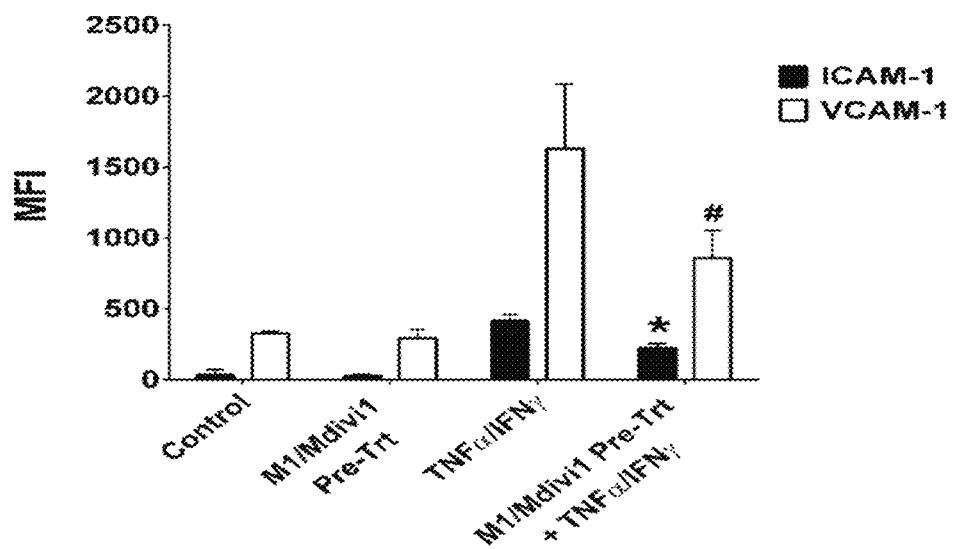

As shown in FIG. 8, 24 hours of pre-treatment with 40 µM/20 µM M1/Mdivi1 reduced the expression of ICAM-1 and VCAM-1 on the surface of activated ECs. As shown with a representative flow cytometry histogram for ICAM-1 (A), and mean fluorescent intensity quantification for both ICAM-1 and VCAM-1 (B). (n=3, *p<0.001, #p<0.01, TNFα/IFNγ vs M1/Mdivi1 Pre-Trt+TNFα/IFNγ).

As shown in the Examples above:
The fusion promoter M1 and the fission inhibitor Mdivi1 exerted effects on ECs, evidenced by mitochondrial elongation.
Forcing mitochondrial fusion and inhibiting fission reduced the expression of adhesion molecules (ICAM-1 and VCAM-1) on EC surface, and decreased the levels of cytotoxic proteins (granzyme B and IFNγ) released by cocultured allogeneic CD8+ T-cells via increasing PD-L1 expression on ECs.

The invention will be further described, without limitation, by the following numbered paragraphs:

1. A formulation to pre-treat an organ prior to transplantation, comprising:
a) a first composition comprising a therapeutically effective amount of compound M1 of formula:

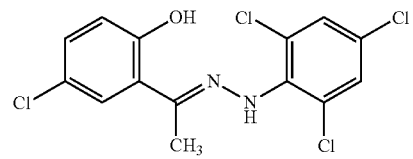 [SMILES: C/C(=N\Nc1c(Cl)cc(Cl)cc1Cl)c1cc(Cl)ccc1O]

and a therapeutically effective amount of compound Mdivi1 of formula:

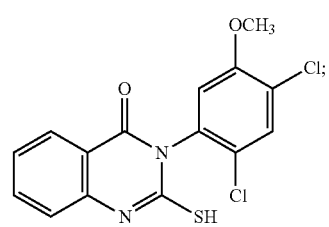 [SMILES: COc1cc(-n2c(S)nc3ccccc3c2=O)c(Cl)cc1Cl]

and
b) a second composition comprising a preservation solution or a warm perfusate.

2. The formulation according to paragraph 1, wherein said preservation solution is selected from the group consisting of Belzer UW Cold Storage Solution, Viaspan, CoStorSol, Kyoto ET Solution, Celsior Solution, Phosphate Buffered Sucrose Solution, Bretschneider Histidine Tryptophan Ketoglutarate (HTK) Solution, Ross-Marshall Citrate Solution, Euro-Collins Solutions and Perferdex, and said warm perfusate is selected from the group consisting of whole blood, blood-based mixtures enhanced with metabolites, any combination of blood components, and Steen solution.

3. A method for pre-treating an organ prior to transplantation, comprising the step of administering to said organ in need thereof a formulation comprising:

a) a first composition comprising a therapeutically effective amount of compound M1 of formula:

[Structure of compound M1: 2-hydroxy-5-chlorophenyl methyl ketone hydrazone with 2,4,6-trichlorophenyl]

and a therapeutically effective amount of compound Mdivi1 of formula:

[Structure of compound Mdivi1: 3-(2,4-dichloro-5-methoxyphenyl)-2-thioxo-quinazolin-4(3H)-one]

and
b) a second composition comprising a preservation solution or a warm perfusate.

4. The method according to paragraph 3, wherein said preservation solution is selected from the group consisting of Belzer UW Cold Storage Solution, Viaspan, CoStorSol, Kyoto ET Solution, Celsior Solution, Phosphate Buffered Sucrose Solution, Bretschneider Histidine Tryptophan Ketoglutarate (HTK) Solution, Ross-Marshall Citrate Solution, Euro-Collins Solutions and Perferdex, and said warm perfusate is selected from the group consisting of whole blood, blood-based mixtures enhanced with metabolites, any combination of blood components, and Steen solution.

5. A kit for producing a formulation to pre-treat an organ prior to transplantation, said kit comprising:
a) a first composition comprising a therapeutically effective amount of compound M1 of formula:

[Structure of compound M1]

and a therapeutically effective amount of compound Mdivi1 of formula:

[Structure of compound Mdivi1]

and
b) a second composition comprising a preservation solution or a warm perfusate.

6. The kit according to paragraph 5, further comprising instructions for use.

7. A method for suppressing or preventing an immune response or organ transplant rejection in a transplant recipient in need thereof, comprising the step of pre-treating an organ prior to transplantation comprising the step of administering to said organ a therapeutically effective amount of a formulation comprising:
a) a first composition comprising a therapeutically effective amount of compound M1 of formula:

[Structure of compound M1]

and a therapeutically effective amount of compound Mdivi1 of formula:

[Structure of compound Mdivi1]

and
b) a second composition comprising a preservation solution or a warm perfusate.

8. A formulation for inducing mitochondrial morphological alterations, comprising:
a therapeutically effective amount of compound M1 of formula:

[Structure of compound M1]

and a therapeutically effective amount of compound Mdivi1 of formula:

[Structure of compound Mdivi1]

9. A formulation, comprising compound M1 of formula:

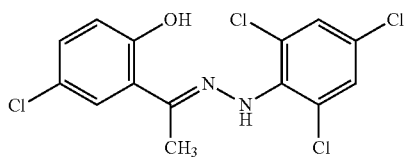 [SMILES: C/C(=N\Nc1c(Cl)cc(Cl)cc1Cl)c1cc(Cl)ccc1O]

and compound Mdivi1 of formula:

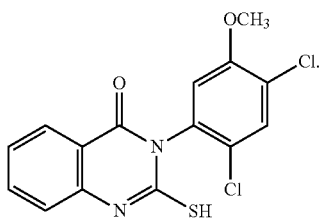 [SMILES: COc1cc(-n2c(S)nc3ccccc3c2=O)c(Cl)cc1Cl]

10. A method for inducing mitochondrial morphological alterations, comprising administering a formulation according to paragraph 8 to a subject in need thereof.

It is to be understood that the invention is not limited to the particular embodiments of the invention described above, as variations of the particular embodiments may be made and still fall within the scope of the appended claims.

What is claimed is:

1. A formulation to pre-treat an organ prior to transplantation, comprising:
   a) a first composition comprising a therapeutically effective amount of compound M1 of formula:

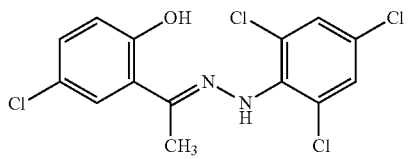 [SMILES: C/C(=N\Nc1c(Cl)cc(Cl)cc1Cl)c1cc(Cl)ccc1O]

and a therapeutically effective amount of compound Mdivi1 of formula:

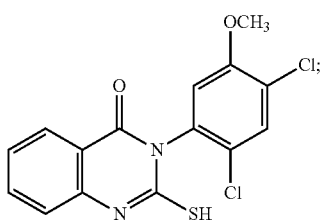 [SMILES: COc1cc(-n2c(S)nc3ccccc3c2=O)c(Cl)cc1Cl]

and
   b) a second composition comprising a preservation solution.

2. A method for pre-treating an organ prior to transplantation, comprising the step of administering to said organ in need thereof a formulation comprising:

a) a first composition comprising a therapeutically effective amount of compound M1 of formula:

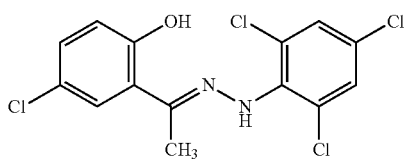 [SMILES: C/C(=N\Nc1c(Cl)cc(Cl)cc1Cl)c1cc(Cl)ccc1O]

and a therapeutically effective amount of compound Mdivi1 of formula:

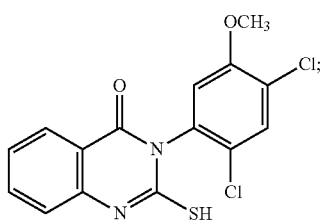 [SMILES: COc1cc(-n2c(S)nc3ccccc3c2=O)c(Cl)cc1Cl]

and
   b) a second composition comprising a preservation solution.

3. A kit for producing a formulation to pre-treat an organ prior to transplantation, said kit comprising:
   a) a first composition comprising a therapeutically effective amount of compound M1 of formula:

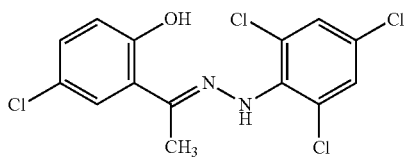 [SMILES: C/C(=N\Nc1c(Cl)cc(Cl)cc1Cl)c1cc(Cl)ccc1O]

and a therapeutically effective amount of compound Mdivi1 of formula:

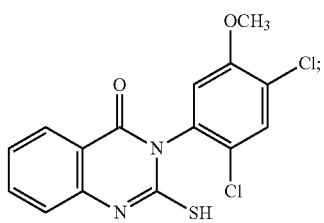 [SMILES: COc1cc(-n2c(S)nc3ccccc3c2=O)c(Cl)cc1Cl]

and
   b) a second composition comprising a preservation solution.

4. The kit according to claim 3, further comprising instructions for use.

5. A method for suppressing or preventing an immune response or organ transplant rejection in a transplant recipient in need thereof, comprising the step of pre-treating an organ prior to transplantation comprising the step of administering to said organ a therapeutically effective amount of a formulation comprising:

a) a first composition comprising a therapeutically effective amount of compound M1 of formula:
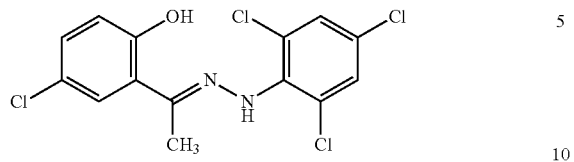
and a therapeutically effective amount of compound Mdivi1 of formula:
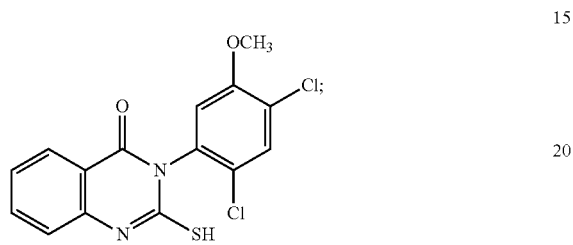
and
b) a second composition comprising a preservation solution.
* * * * *